United States Patent [19]

McShane

[11] 4,434,154

[45] Feb. 28, 1984

[54] TANNING AND ULTRA-VIOLET SCREENING COMPOSITION HAVING HIGH STABILITY

[75] Inventor: James E. McShane, Memphis, Tenn.

[73] Assignee: Plough, Inc., Memphis, Tenn.

[21] Appl. No.: 371,101

[22] Filed: Apr. 23, 1982

Related U.S. Application Data

[63] Continuation of Ser. No. 228,403, Jan. 26, 1981, abandoned.

[51] Int. Cl.$^3$ ................................................ A61K 7/44
[52] U.S. Cl. ........................................ 424/60; 424/63
[58] Field of Search ..................................... 424/60, 63

[56] References Cited

U.S. PATENT DOCUMENTS 4,193,989  3/1980  Teng et al. ............................ 424/60

FOREIGN PATENT DOCUMENTS 881336  11/1961  United Kingdom ................. 424/59

OTHER PUBLICATIONS

Blau et al., Archives of Dermatology, 1960, vol. 82, pp. 501 and 502.
Cosmetics & Toiletries, 3/1976, vol. 91 pp. 89 to 94.
American Perfumes and Cosmetics 5/1957 pp. 33 to 35.
Ash, A Formulary of Cosmetic Preparations, 1977, pp. 381, 388, 387, 386.

*Primary Examiner*—Dale R. Ore
*Attorney, Agent, or Firm*—Robert S. Salzman; Bruce M. Eisen

[57] ABSTRACT

Cosmetic compositions for imparting artificial tan to human skin and shielding the skin from ultra-violet rays comprising dihydroxy acetone, octyl dimethyl PABA, water, oil, and surfactant. The composition has pH after compounding between 2.9 and 5.

6 Claims, No Drawings

TANNING AND ULTRA-VIOLET SCREENING COMPOSITION HAVING HIGH STABILITY

This is a continuation of U.S. application Ser. No. 228,403, filed Jan. 26, 1981, now abandoned.

This invention relates to cosmetic compositions capable of imparting artificial tan to human skin and to shielding the skin from harmful ultra-violet rays.

U.S. Pat. No. 3,177,120 describes a composition containing dihydroxy acetone and homomenthyl salicylate. This prior-art composition imparts an artificial tan and shields the skin from ultra-violet rays, but is found to develop a disagreeable odor upon prolonged storage, i.e. 12 months. Even high amounts of expensive perfume are not capable of masking the odor that eventually develops. Another disadvantage of the prior-art compositions is that conventional dyes and pigments are not stable therein upon prolonged storage.

The present invention, which also imparts artificial tan and shields the skin, may be stored for much longer periods than the prior art composition without developing disagreeable odor. Furthermore, perfume need not be used. If a particular scent is desired for the composition, it may be imparted by using much less perfume than required for the prior-art compositions. This is particularly advantageous to those individuals having skin sensitivity to such ingredients. Another advantage is that dyes and pigments are not degraded upon prolonged storage.

SUMMARY OF THE INVENTION

The present invention comprises:

A cosmetic composition, stable after prolonged storage, capable of imparting artificial tan to human skin and of at least partially shielding the skin from ultra-violet rays comprising, based on the total weight of the composition:
(a) 2.5 to 7.5 percent dihydroxy acetone,
(b) 1.5 to 9 percent octyl dimethyl PABA,
(c) water,
(d) oil, and
(e) surfactant,
wherein said composition has pH after compounding between 2.9 and 5.0.

Varying the amount of octyl dimethyl PABA varies the amount of ultra-violet protection. Hence, different amounts of protection from ultra-violet rays may be achieved as desired.

Terms used to describe ingredients in the compositions conform to those of the CTFA Cosmetic Ingredient Dictionary, Second Edition, published by The Cosmetic, Toiletry and Fragrance Association, Inc., 1133 Fifteenth Street, N.W., Washington, D.C. 20005. The relevant contents of this dictionary are incorporated herein by reference.

Unless stated otherwise, all percents are weight percents based on the total weight of the composition.

DETAILED DESCRIPTION OF THE INVENTION

This invention is predicated on the discovery that certain compositions comprising a particular combination of artificial tanning agent and sunscreen, generally believed unstable by those in the art, has a surprisingly high stability. For example, U.S. Pat. No. 3,177,120 advises against combining dihydroxy acetone and sunscreens containing amino groups. However, when dihydroxy acetone and octyl dimethyl PABA are combined in accordance with the present invention, increased stability results. Octyl dimethyl PABA contains an amino group, which is surprisingly inactive with regard to dihydroxy acetone.

The individual ingredients of the inventive compositions are described below.

The composition must contain dihydroxy acetone to impart artificial tan to human skin. The amount used will depend on the amount of artificial tan desired. From 2.5 to 7.5 percent dihydroxy acetone is preferable, with 3.5 percent to 5 percent being more preferable.

For shielding the skin from harmful ultra-violet rays the compositions contain octyl dimethyl PABA [octyl-p-(dimethyl-amino)benzoate], also known as Padimate O, available as Escalol 507 from Van Dyk, Belleville, N.J. The amount of sunscreen used will depend on the amount of protection from ultra-violet rays desired. At least 1.5 percent octyl dimethyl PABA is required for minimum protection while promoting natural tan. The maximum amount may be as high as 9 percent. About 1.5 to 6 percent is preferred, and 1.5 to 4 percent is more preferable.

Surprisingly, the octyl dimethyl PABA and dihydroxy acetone do not react with each other within the inventive composition upon prolonged storage.

The compositions preferably contain preservatives compatible with dihydroxy acetone in amounts effective for preventing degradation by microorganisms. Methyl paraben and propyl paraben are preferred.

The compositions are preferably oil-in-water emulsions, preferably containing 80 to 95 percent, more preferably from 85 to 92 percent water. Although ordinary tap water may be suitable in some localities, it is preferable to use water purified by deionization, etc.

The compositions preferably contain from 1 to 6 percent oil, more preferably from 2 to 4 percent oil. Saturated alcohols having from 10 to 20 carbon atoms are acceptable. The most preferable oil is a combination of cetyl alcohol and stearyl alcohol.

Surfactant must be present to avoid separation of the oil and water. Preferable surfactants are sodium alkyl sulfates wherein the alkyl group contains from 8 to 16 carbon atoms. The most preferred surfactant is sodium lauryl sulfate. The surfactant may constitute from 0.1 to 1 percent of the composition, more preferably from 0.3 to 0.5 percent.

Optional additional ingredients include perfume and color. From 0.05 to 0.5 percent perfume, or more can be used. However the perfume may be omitted because, unlike prior-art compositions, the inventive compositions do not develop disagreeable odors upon prolonged storage. Dyes and pigments may be included. These colors are stable in the compositions after prolonged storage, which is not true for prior-art compositions.

A further optional ingredient is dimethicone, for example, Medical Fluid 360 sold by Dow Corning. The dimethicone preferably contains 200 to 350 slicone atoms. From 0.01 to 1 percent dimethicone is acceptable.

EXAMPLE

Tanning and ultra-violet screening compositions in accordance with the invention are prepared as follows:

| | | AMOUNTS (Weight Percents) | | | |
|---|---|---|---|---|---|
| | INGREDIENT | 1 | 2 | 3 | 4 |
| Part I | Water | q.s. to 100 Percent | | | |
| | Sodium Lauryl Sulfate | 0.4 | 0.4 | 0.4 | 0.4 |
| | Methyl Paraben | 0.1 | 0.1 | 0.1 | 0.1 |
| | Propyl Paraben | 0.03 | 0.03 | 0.03 | 0.03 |
| | Color and Perfume | 3.0 | — | — | 3.0 |
| | Dihydroxy Acetone | 3.5 | 3.5 | 5.0 | 5.0 |
| Part II | Octyl Dimethyl PABA | 1.5 | 1.5 | 1.5 | 1.5 |
| | Dimethicone | 0.4 | 0.4 | 0.4 | 0.4 |
| | Stearyl Alcohol | 0.625 | 0.625 | 0.625 | 0.625 |
| | Cetyl Alcohol | 2.5 | 2.5 | 2.5 | 2.5 |
| | | 100 | 100 | 100 | 100 |

Part I is formed by heating the water to 70° C. and dissolving the other ingredients for Part I therein.

Part II is formed by blending the ingredients and heating to 70° C.

At 70° C. Parts I and II are combined and mixed well to form an oil in water emulsion. The emulsion is cooled to room temperature. The pH is between 2.9 and 5 for all examples.

For commercial use, these compositions are preferably packaged in containers that shield them from ultra-violet light.

The resulting compositions are found to have the following advantages over prior-art compositions containing dihydroxy acetone and homomenthyl salicylate:

1. They are stable upon prolonged storage without developing a disagreeable odor.
2. Less sunscreen need be used, because the octyl dimethyl PABA is effective in lower concentrations than homomenthyl salicylate.
3. The compositions have less odor and may be compounded without perfume. If perfume is desired, smaller amounts are necessary to impart the desired scent.
4. The compositions are more economical because they contain smaller amounts of expensive ingredients such as sunscreens and perfumes, and may therefore contain higher amounts of water.
5. Optional dyes and pigments are stable in the inventive compositions, even upon prolonged storage.

What is claimed is:

1. A cosmetic composition capable of imparting artificial tan to human skin and of at least partially shielding the skin from ultra-violet rays comprising, based on the total weight of the composition:
   (a) 2.5 to 7.5 percent dihydroxy acetone,
   (b) 1.5 to 6 percent octyl dimethyl PABA,
   (c) 80 to 95 percent water,
   (d) 1 to 6 percent oil, and
   (e) 0.1 to 1 percent surfactant,
said composition being an oil in water emulsion, stable after prolonged storage without developing disagreeable odor.

2. The composition of claim 1 containing:
   (a) 3.5 to 5 percent dihydroxy acetone,
   (b) 1.5 to 4 percent octyl dimethyl PABA,
   (c) 85 to 92 percent water,
   (d) 2 to 4 percent oil, and
   (e) 0.3 to 0.5 percent surfactant.

3. The composition of claim 1:
   wherein said oil is selected from the group consisting of cetyl alcohol, stearyl alcohol and combinations thereof, and said surfactant is sodium lauryl sulfate.

4. The composition of claim 1 containing:
   (a) 3.5 to 5 percent dihydroxy acetone,
   (b) 1.5 to 4 percent octyl dimethyl PABA,
   (c) 85 to 92 percent water,
   (d) 2 to 4 percent oil,
wherein said oil is a combination of cetyl alcohol and stearyl alcohol,
   (e) from 0.3 to 0.5 percent surfactant,
wherein said surfactant is sodium lauryl sulfate, and further comprising,
   (f) from 0.1 to 1 percent dimethicone.

5. The composition of claim 4 further comprising at least one additional ingredient selected from the group consisting of preservative, color, and perfume.

6. An article for commerce comprising the composition of claim 1 packaged in an ultra-violet-light-shielding container.

* * * * *

UNITED STATES PATENT AND TRADEMARK OFFICE
CERTIFICATE OF CORRECTION

PATENT NO. : 4,434,154
DATED : Feb. 28, 1984
INVENTOR(S) : James E. McShane

It is certified that error appears in the above—identified patent and that said Letters Patent is hereby corrected as shown below:

On the cover page, left column below "4,193,989  3/1980 Teng et al. .......... 424/60", add the following:

"4,172,122  10/79  Kubik et al. ............ 424/59
3,403,207   9/68  Kreps et al. ............ 424/60
3,177,120   4/65  Black et al. ............ 167/90"

Signed and Sealed this

Tenth Day of October, 1989

Attest:

DONALD J. QUIGG

Attesting Officer

Commissioner of Patents and Trademarks